(12) United States Patent
Steffens et al.

(10) Patent No.: US 7,931,877 B2
(45) Date of Patent: Apr. 26, 2011

(54) NEEDLELESS HUB DISINFECTION DEVICE

(75) Inventors: Jeffrey B. Steffens, Cary, IL (US); Gregory T. Davis, Crystal Lake, IL (US); Paul H. Hanifl, Barrington Hills, IL (US)

(73) Assignee: Sage Products, Inc., Cary, IL (US)

( * ) Notice: Subject to any disclaimer, the term of this patent is extended or adjusted under 35 U.S.C. 154(b) by 706 days.

(21) Appl. No.: 11/877,301

(22) Filed: Oct. 23, 2007

(65) Prior Publication Data

US 2008/0095680 A1 Apr. 24, 2008

Related U.S. Application Data

(63) Continuation-in-part of application No. 11/132,902, filed on May 19, 2005, now Pat. No. 7,682,561.

(51) Int. Cl.
| | |
|---|---|
| A61L 2/00 | (2006.01) |
| B08B 9/00 | (2006.01) |
| B08B 9/027 | (2006.01) |
| B08B 9/20 | (2006.01) |
| A61M 5/178 | (2006.01) |
| A61M 5/32 | (2006.01) |

(52) U.S. Cl. ............. 422/292; 422/1; 422/28; 422/302; 134/22.1; 134/22.11; 134/22.13; 134/22.17; 134/25.4; 134/166 R; 134/168 C; 134/167 C; 604/905; 604/164.04; 604/199

(58) Field of Classification Search ................ 422/1, 28, 422/292, 302; 134/22.1, 22.11, 22.13, 22.17, 134/25.4, 166 R, 168 C, 167 C; 604/905, 604/164.04, 199

See application file for complete search history.

(56) References Cited

U.S. PATENT DOCUMENTS

| | | | | |
|---|---|---|---|---|
| 4,417,890 A | * | 11/1983 | Dennehey et al. | ............ 604/256 |
| 4,440,207 A | * | 4/1984 | Genatempo et al. | ........... 150/154 |
| 5,620,424 A | * | 4/1997 | Abramson | .................... 604/265 |

* cited by examiner

*Primary Examiner* — Jill Warden
*Assistant Examiner* — Monzer R Chorbaji
(74) *Attorney, Agent, or Firm* — Barnes & Thornburg LLP

(57) ABSTRACT

A device for disinfecting a portion of an implement such as a needleless hub or injection port. The device includes a body shaped to engage the implement with the portion to be disinfected exposed. A disinfectant area is located on the body so as to permit pivotal displacement of the area relative to the body such that in a first orientation the portion to be disinfected is exposed and in a second orientation the portion to be disinfected is covered and the disinfectant area engages the portion to be disinfected.

19 Claims, 3 Drawing Sheets

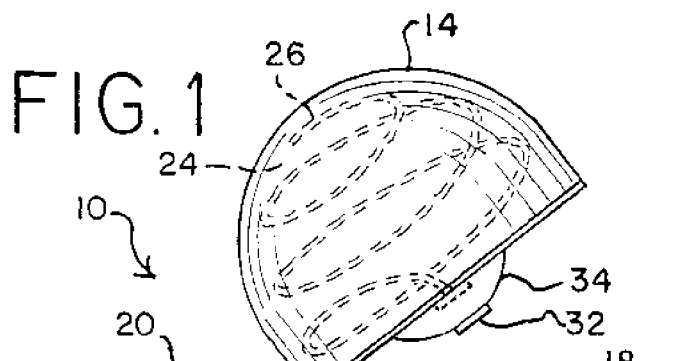
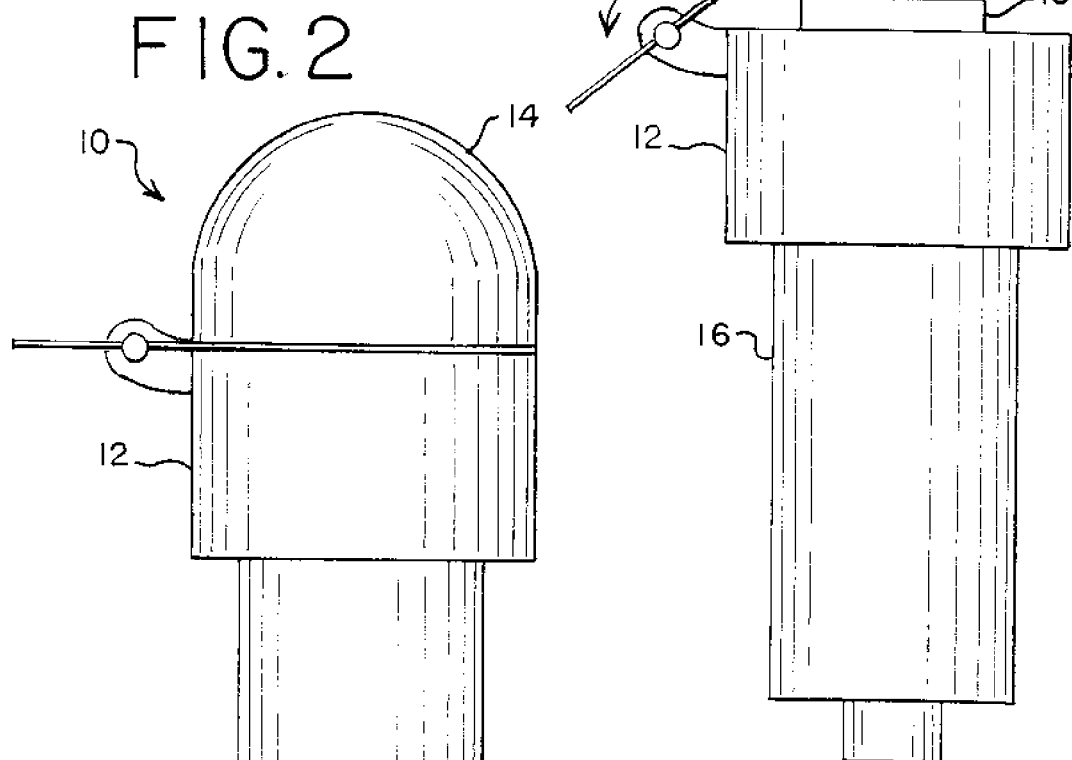
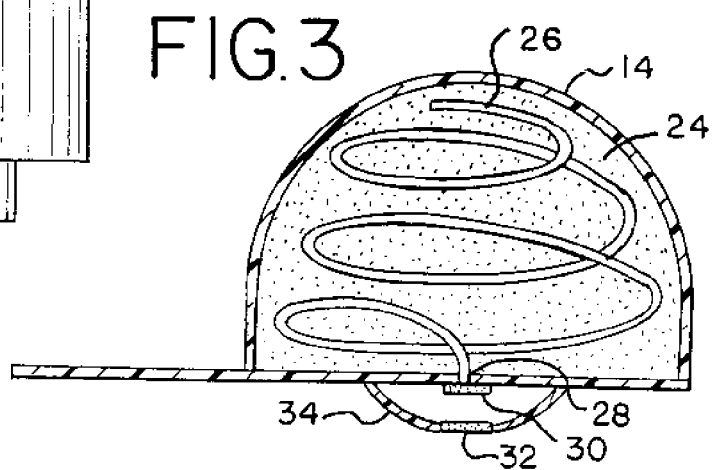

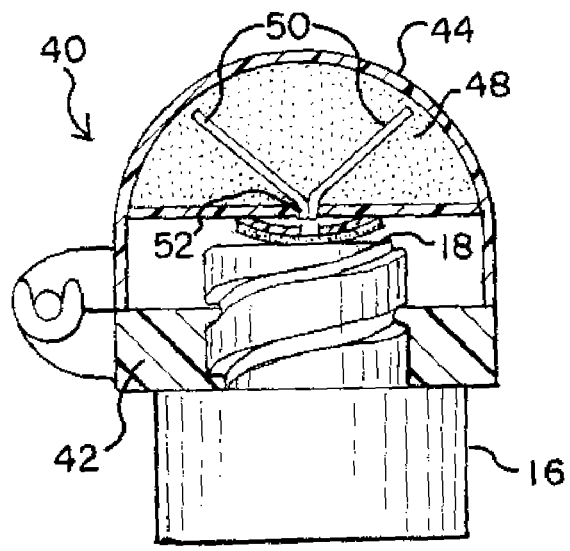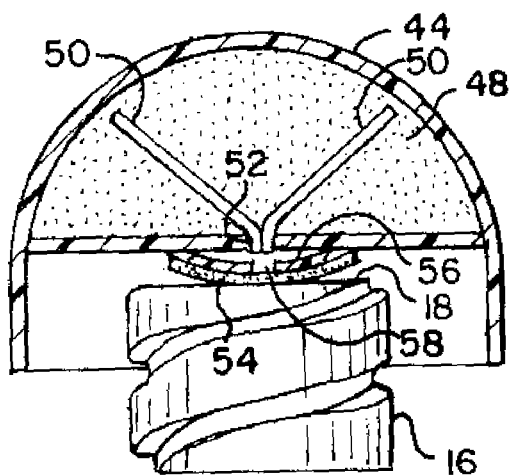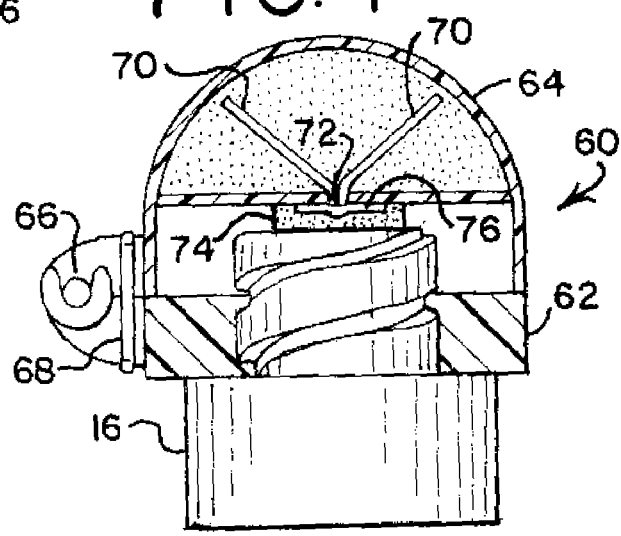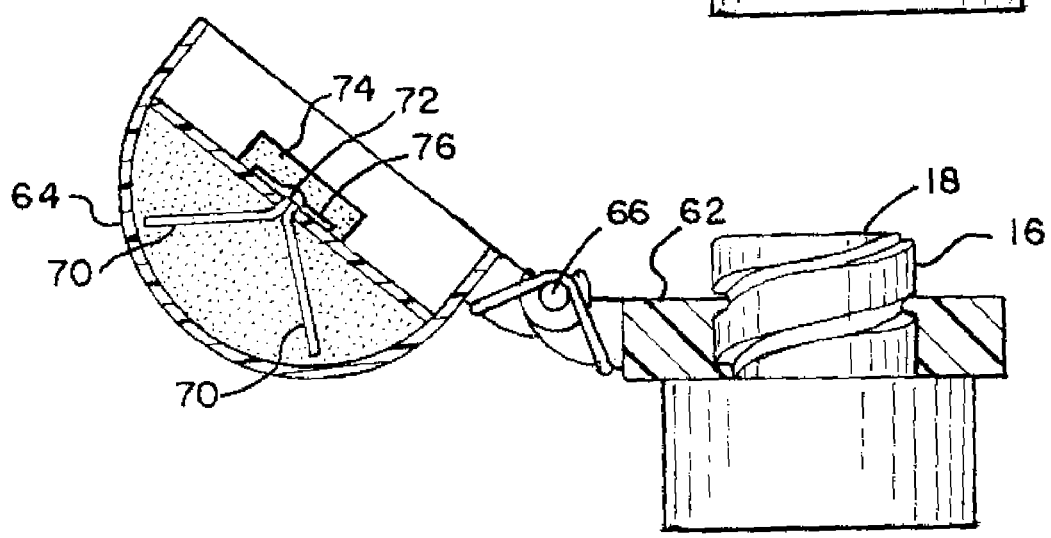

NEEDLELESS HUB DISINFECTION DEVICE

RELATED APPLICATION

This application is a continuation-in-part of U.S. patent application Ser. No. 11/132,902, filed May 19, 2005 now U.S. Pat. No. 7,682,561.

BACKGROUND OF THE INVENTION

This invention relates to medical implements or the like such as needleless hubs or injection ports, and in particular to a device for disinfecting a portion of the medical implement and which keeps the hub and/or port covered, clean and disinfected.

Needleless vascular catheter hubs and access or injection ports are used thousands of times each day in the United States medical facilities. Unless the hubs and ports are disinfected, patients are at a significant risk of blood stream infections caused by microbes that gain access through the needleless hub or injection port.

In the past, practitioners using a needleless hub or injection port have sought to disinfect the hub or port with alcohol in order to prevent microbial entry. Practitioners who seek disinfection in this manner typically wipe the hub or injection port with an alcohol-soaked swab before accessing it. That, however, has proven to be only partially successful in reducing blood stream infections which are introduced through the needleless hubs or injection ports.

U.S. Pat. Nos. 5,554,135, 5,792,120 and 6,045,539 deal with the infection problem by providing a cover for the injection port, with the cover including a sponge and shatterable plastic capsule containing an antiseptic solution. When the cover is applied to a needleless hub or injection port and the plastic capsule is shattered, disinfectant soaks the sponge and disinfects the covered end of the needleless hub or injection port. This is a one-time use device.

U.S. patent application Ser. No. 11/132,902, the disclosure of which is incorporated by reference, provides a device having automatic hub disinfection once the disinfectant pad is displaced.

SUMMARY OF THE INVENTION

The invention is directed to a device for disinfecting a portion of an implement, such as a needleless hub or injection port, and comprises a body shaped to engage the implement with the portion to be disinfected exposed. A disinfectant area is associated with the body, and a mounting is provided for the disinfectant to permit displacement of the disinfectant area relative to the body, such that in a first orientation the portion to be disinfected is exposed and in a second orientation the portion to be disinfected is covered and the disinfectant area engages the portion to be disinfected.

In accordance with one form of the invention, the body includes a threaded portion shaped to engage a threaded portion of the implement. In another form of the invention, the body can be otherwise affixed to the implement.

In the preferred form of the invention, a cap is pivotally connected to the body, with the disinfectant area being mounted in the cap. The cap includes a disinfectant reservoir having an orifice. A wick may be provided in the reservoir leading to the orifice. The disinfectant area is located proximate and in communication with the orifice.

In one form of the invention, the disinfectant area is secured to a film mounted about the orifice. The wick extends through the orifice to a second orifice in the film, the second orifice communicating with the disinfectant area.

In another form of the invention, the disinfectant area is in the form of a pad secured over the first orifice, preferably with an adhesive. The adhesive is apertured or otherwise formed such that there is fluid communication through the adhesive to the disinfectant area.

BRIEF DESCRIPTION OF THE DRAWINGS

The invention is described in greater detail in the following description of examples embodying the best mode of the invention, taken in conjunction with the drawing figures, in which:

FIG. 1 is a side elevation illustration of one form of the invention, partially in cross-section and showing the cap open, FIG. 2 is a side elevational illustration similar to FIG. 1, but with the cap closed, FIG. 3 is an enlarged cross-sectional view of the cap shown in FIGS. 1 and 2, FIG. 4 is a cross-sectional illustration of a second form of the invention when mounted upon a medical implement, with the cap closed, FIG. 5 is an enlarged illustration of a portion of the invention illustrated in FIG. 4 in order to show detail, FIG. 6 is a side elevational illustration, partially in cross-section, of another form of the invention with the cap open, FIG. 7 is a view similar to FIG. 6, but with the cap closed.

DESCRIPTION OF EXAMPLES EMBODYING THE BEST MODE OF THE INVENTION

Figure 8:
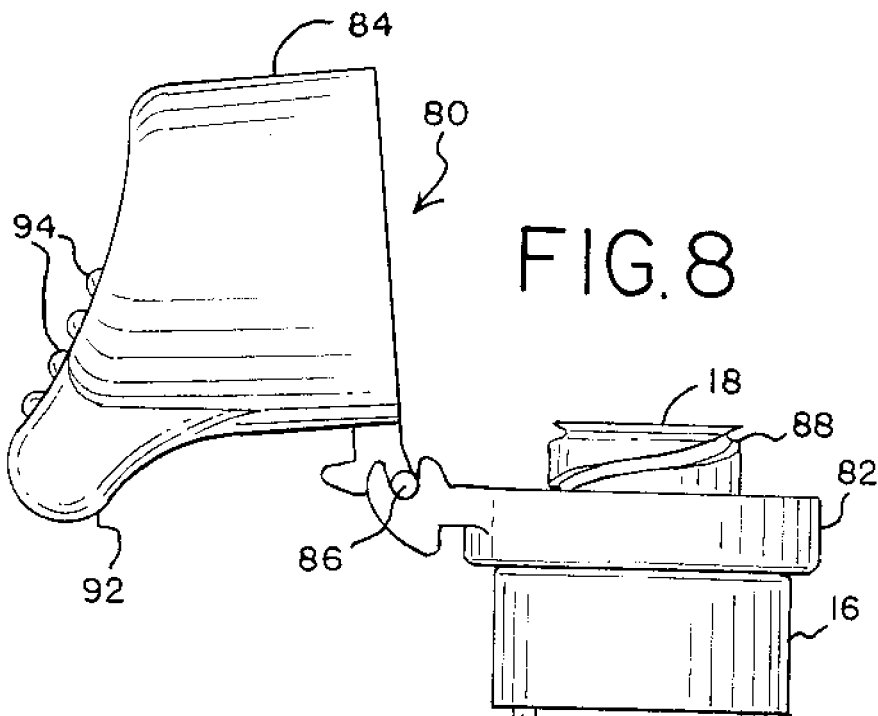
FIG. 8 is an elevation view of another form of the invention, mounted on a medical implement.

A first form of the device according to the invention is shown in FIGS. 1-3. The device 10 includes two primary components, a body 12 and a cap 14.

The body 12 is shaped to engage an implement such as a medical implement 16, the medical implement 16 preferably comprising a needleless hub or injection port. The body 12 includes a central aperture, as best shown in other forms of the invention, through which the medical implement 16 extends. Typically, the medical implement 16 is topped with a head 18, through which access is provided, either for withdrawing fluid or injection therewithin to a vascular catheter (not illustrated) connected to the medical implement 16 in a conventional fashion. The medical implement 16 and its use are well known in the art, and are therefore not described in greater detail.

The cap 14 is mounted on the body for pivotal displacement, as depicted by the arrow 20 in FIG. 1. A hinge 22 can be employed, or any other suitable means of pivotal displacement. While not shown in this embodiment, preferably the cap 14 is biased closed over the head 18.

The cap 14 includes a reservoir 24 filled with an appropriate solution, the nature of which is not part of the present invention. The reservoir may contain a disinfectant, antimicrobial solution or similar type of fluid. If needed, a wick 26 is located in the reservoir 24, leading to and through an orifice 28 to a pad 30 mounted exterior of the reservoir 24. A disinfectant area 32 is located on a flexible film 34, with a further orifice extending through the film 34 to the disinfectant area 32. The disinfectant area 32 may be a pad or any other means of disinfecting or having anti-microbial properties. Thus, "disinfectant" is used to mean any means of disinfecting or providing antimicrobial effect. When the cap is closed to the position shown in FIG. 2, the flexible film 34 is displaced toward the reservoir 24, and fluid from the reservoir 24 is communicated to the disinfectant area 32 and thus to the head 18, thereby disinfecting the head 18.

A second form of the invention is shown in FIGS. 4 and 5. The device 40, similar to the device 10, includes a body 42 and a cap 44. The body 42 is shaped to engage the medical implement 16 in the same manner as the first form of the invention, and a hinge 46 is provided for pivotal displacement of the cap 44 relative to the body 42. Like the first form of the invention, preferably the cap 44 is biased closed over the head 18.

In this form of the invention, the cap 44 includes a reservoir 48. If needed, a wick 50 extends in the reservoir 48 to and through an orifice 52. A disinfectant area 54 is located on a flexible film 56 mounted above the orifice 52. One or more orifices 58 extend through the film 56 to the disinfectant area 54, providing fluid communication to the disinfectant area 54 from the disinfectant reservoir 48. Thus, when the cap 44 is closed as illustrated in FIGS. 4 and 5, the disinfectant area 54 engages and disinfects the head 18.

Another form of the invention, similar to that of FIGS. 4 and 5, is illustrated in FIGS. 6 and 7. In this form of the invention, the device 60 includes a body 62 and a cap 64, with a hinge 66 providing pivotal connection between the cap 64 and the body 62. The cap 64 is biased closed over the head 18 by means of an elastic band 68, similar to a rubber band, or any other means of returning the cap 64 to a closed orientation.

The cap 64 includes a reservoir, filled with an appropriate fluid, and having wicks 70, if necessary, leading to and through an orifice 72. A disinfectant area 74 is secured over the orifice 72 by means of an adhesive 76. The adhesive 76 may be any suitable adhesive which does not react with the disinfectant fluid in the reservoir 68, and is appropriately apertured so that there is fluid communication through the orifice 72 to the disinfectant area 74. For example, if the adhesive 76 is a hot melt adhesive, once the adhesive as solidified, it can be pierced through the disinfectant area 74 to the orifice 72 to provide fluid communication. As in all forms of the invention, when the cap 64 is closed, the disinfectant area 74, which is bathed in the fluid from the reservoir 68, disinfects the head 18.

Figure 9:
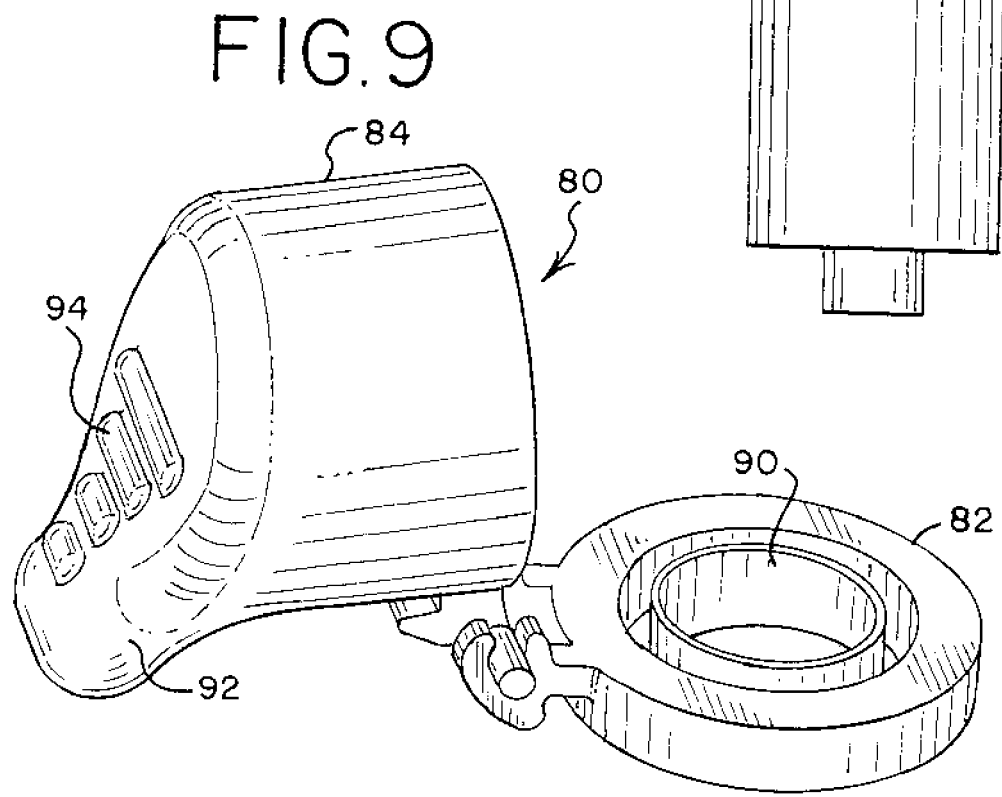
FIG. 9 is a perspective view of the form of the invention shown in FIG. 8.

A slightly different form of the invention, in relation to the shape of the cap, only, is shown in FIGS. 8 and 9. The device 80 includes a body 82 and a cap 84, with a hinge 86 for pivotal displacement of the cap 84 relative to the body 82.

The body 82 is shaped to fit on the medical implement 16, and as shown in FIG. 8, the medical implement 16 typically includes an external thread 88. Similarly, the body 82 includes a conforming aperture 90 with appropriate internal threading to engage the threads 88.

The cap 84 is shaped for ease of manipulation. To this end, the cap 84 may include an integral thumb extension 92 with appropriate knurling 94, as shown. The exterior of the cap 84 can be formed as desired in order to contain the fluid reservoir described above and permit ease of manipulation.

The invention provides several advantages. It may fit on many different medical implements, and can be universal in nature. It can be both detachably attached the medical implement, or permanently attached. Because of the relatively large fluid reservoir in relation to the outlet orifice from the reservoir, the device is passive, and the disinfectant area is always prepped and ready to disinfect the head 18 once the cap is closed. The sizes of the orifices depend on the viscosity of the fluid, as well as its surface tension. While a single orifice has been shown and described leading from the fluid reservoir, there could be multiple orifices, as appropriate.

While a fluid is used to provide efficacy for the disinfectant area, other means may be used, as well. Rather than activation by a fluid, the disinfectant area can be a solid, such as a material containing silver for antimicrobial effect, and the fluid can be omitted. Other appropriate solids can be used, as well, to provide the desired "disinfecting".

Various changes can be made to the invention without departing from the spirit thereof or scope of the following claims.

What is claimed is:

1. A device for disinfecting a portion of an implement comprising:
    a. a body shaped to engage the implement with the portion to be disinfected exposed;
    b. a disinfectant area associated with said body,
    c. a mounting for said disinfectant area to permit displacement of said disinfectant area relative to said body, such that in a first orientation the portion to be disinfected is exposed and in a second orientation the portion to be disinfected is covered and said disinfectant area engages the portion to be disinfected, and
    d. including a cap pivotally connected to said body, said disinfectant area being located in said cap, said cap being biased in a closed orientation, said cap including a reservoir having an orifice, and including a wick in said reservoir leading into said orifice, said disinfectant area being located proximate and in communication with said orifice, said disinfectant area being located on a film mounted about said orifice, said wick extending through said orifice to a second orifice in said film, said second orifice communicating with said disinfectant area.

2. The device according to claim 1, in which said body includes a threaded portion shaped to engage a threaded portion of the medical implement.

3. The device according to claim 1, in which said disinfectant area is located about said orifice.

4. The device according to claim 3 in which said disinfectant area comprising a pad secured with an adhesive.

5. The device according to claim 4, including fluid communication through said adhesive to said pad.

6. A device for disinfecting a portion of a medical implement, comprising:
    a. a body shaped to engage the medical implement with the portion to be disinfected exposed;
    b. a cap having a pivotal connection to said body, said cap including a fluid reservoir having at least one orifice,
    c. a disinfectant area in said cap located proximate and in communication with said orifice, said disinfectant area being located on a film mounted about said orifice, and including a wick which extends through said orifice to a second orifice in said film, said second orifice communicating with said disinfectant area, and
    d. said pivotal connection comprising a hinge formed to permit pivotal displacement of said cap relative to said body, such that in a first orientation the portion to be disinfected is exposed and in a second orientation the portion to be disinfected is covered and said disinfectant area engages the portion to be disinfected.

7. The device according to claim 6, in which said disinfectant area is located about said orifice.

8. The device according to claim 7, in which said disinfectant area is secured with an adhesive.

9. A device for disinfecting a portion of an implement comprising:

a. a body shaped to engage the implement with the portion to be disinfected exposed;
b. a disinfectant area associated with said body,
c. a mounting for said disinfectant area to permit displacement of said disinfectant area relative to said body, such that in a first orientation the portion to be disinfected is exposed and in a second orientation the portion to be disinfected is covered and said disinfectant area engages the portion to be disinfected, and
d. a cap pivotally connected to said body, said disinfectant area being located in said cap, said cap including a reservoir having an orifice, and including a wick in said reservoir leading into said orifice, said disinfectant area being located proximate and in communication with said orifice, said wick extending through said orifice to a second orifice in said disinfectant area, said second orifice communicating with said disinfectant area.

10. The device according to claim 9, in which said body includes a threaded portion shaped to engage a threaded portion of the medical implement.

11. The device according to claim 9, in which said cap is biased in a closed orientation.

12. The device according to claim 9, in which said disinfectant area is located on a film mounted about said orifice.

13. The device according to claim 9, in which said disinfectant area is located about said orifice.

14. The device according to claim 13 in which said disinfectant area comprising a pad secured with an adhesive.

15. The device according to claim 14, including fluid communication through said adhesive to said pad.

16. A device for disinfecting a portion of a medical implement, comprising:
a. a body shaped to engage the medical implement with the portion to be disinfected exposed;
b. a cap having a pivotal connection to said body, said cap including a fluid reservoir having at least one orifice, and
c. a disinfectant area in said cap located proximate and in communication with said orifice, said disinfectant area being located on a film mounted about said orifice, and including a wick which extends through said orifice to a second orifice in said film, said second orifice communicating with said disinfectant area.

17. The device according to claim 16, in which said pivotal connection comprises a hinge formed to permit pivotal displacement of said cap relative to said body, such that in a first orientation the portion to be disinfected is exposed and in a second orientation the portion to be disinfected is covered and said disinfectant area engages the portion to be disinfected.

18. The device according to claim 16, in which said disinfectant area is located about said orifice.

19. The device according to claim 18, in which said disinfectant area is secured with an adhesive.

\* \* \* \* \*